(12) United States Patent
Acevedo et al.

(10) Patent No.: US 12,011,183 B2
(45) Date of Patent: *Jun. 18, 2024

(54) SURGICAL DRILL GUIDE

(71) Applicant: Arthrex, Inc., Naples, FL (US)

(72) Inventors: Jorge Acevedo, Naples, FL (US); Peter Mangone, Naples, FL (US); Zachary Day, Naples, FL (US); James McWilliam, Rye, NY (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/060,195

(22) Filed: Oct. 1, 2020

(65) Prior Publication Data
US 2021/0015498 A1 Jan. 21, 2021

Related U.S. Application Data

(63) Continuation of application No. 15/795,109, filed on Oct. 26, 2017, now Pat. No. 10,792,052.

(51) Int. Cl.
| | |
|---|---|
| *A61B 17/16* | (2006.01) |
| *A61B 17/00* | (2006.01) |
| *A61B 17/17* | (2006.01) |
| *A61B 17/32* | (2006.01) |
| *A61B 17/34* | (2006.01) |
| *A61B 90/00* | (2016.01) |

(52) U.S. Cl.
CPC ...... *A61B 17/1697* (2013.01); *A61B 17/1682* (2013.01); *A61B 17/17* (2013.01); *A61B 17/1775* (2016.11); *A61B 17/1796* (2013.01); *A61B 2017/00429* (2013.01); *A61B 17/1615* (2013.01); *A61B 17/320016* (2013.01); *A61B 2017/320052* (2013.01); *A61B 17/3421* (2013.01); *A61B 2090/033* (2016.02)

(58) Field of Classification Search
CPC . A61B 17/17; A61B 17/1615; A61B 17/1671; A61B 17/1757; A61B 17/1697; A61B 17/1796; A61B 17/3421; A61B 17/320016; A61B 17/1775; A61B 17/1682; A61B 2017/320044; A61B 2017/320052
USPC ................................................. 606/96, 170
See application file for complete search history.

(56) References Cited

U.S. PATENT DOCUMENTS

| | | | |
|---|---|---|---|
| 5,112,337 A | * | 5/1992 | Paulos ............... A61B 17/1764 606/98 |
| 5,139,520 A | | 8/1992 | Rosenberg |
| 5,320,626 A | | 6/1994 | Schmieding |
| 5,342,369 A | | 8/1994 | Harryman, II |
| 5,489,284 A | * | 2/1996 | James ................ A61B 17/8872 606/62 |
| 5,584,839 A | | 12/1996 | Gieringer |
| 5,681,333 A | | 10/1997 | Burkhart et al. |
| 5,690,677 A | | 11/1997 | Schmieding et al. |
| 5,700,266 A | | 12/1997 | Harryman |
| 5,948,002 A | | 9/1999 | Bonutti |
| 5,951,559 A | | 9/1999 | Burkhart |
| 6,013,083 A | | 1/2000 | Bennett |

(Continued)

*Primary Examiner* — Marcela I. Shirsat
(74) *Attorney, Agent, or Firm* — Carlson, Gaskey & Olds, P.C.

(57) ABSTRACT

Drill guides are disclosed herein that include a tapered projection that hooks under a bone to position the drill guide relative to the bone. The drill guide is used to drill a hole that receives a suture anchor.

20 Claims, 4 Drawing Sheets

(56) References Cited

U.S. PATENT DOCUMENTS

| | | | |
|---|---|---|---|
| 6,371,968 B1* | 4/2002 | Kogasaka | A61B 17/3417 606/86 R |
| 6,490,467 B1 | 12/2002 | Bucholz et al. | |
| 7,131,974 B2* | 11/2006 | Keyer | A61B 17/17 606/96 |
| 7,204,839 B2 | 4/2007 | Dreyfuss | |
| 8,277,458 B2 | 10/2012 | Schneider | |
| 8,801,727 B2 | 8/2014 | Chan et al. | |
| 10,792,052 B2* | 10/2020 | Acevedo | A61B 17/1682 |
| 2002/0068911 A1 | 6/2002 | Chan | |
| 2004/0073227 A1* | 4/2004 | Dreyfuss | A61B 17/1778 606/96 |
| 2010/0121337 A1 | 5/2010 | Pandya | |
| 2011/0166608 A1* | 7/2011 | Duggal | A61B 17/7291 606/328 |
| 2013/0012953 A1 | 1/2013 | Chan et al. | |
| 2014/0188139 A1 | 7/2014 | Fallin et al. | |
| 2017/0014172 A1* | 1/2017 | Fallin | A61B 17/8861 |
| 2018/0042631 A1 | 2/2018 | Garlock et al. | |

\* cited by examiner

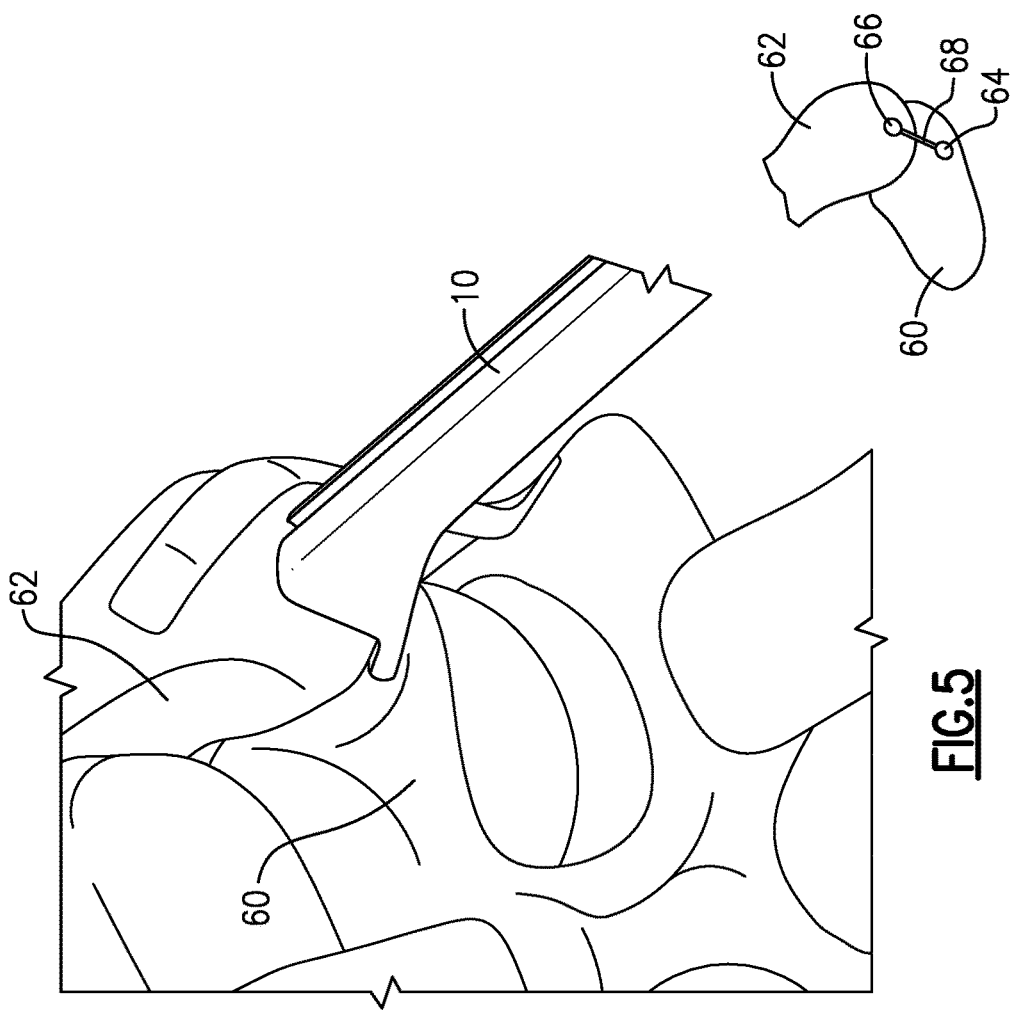
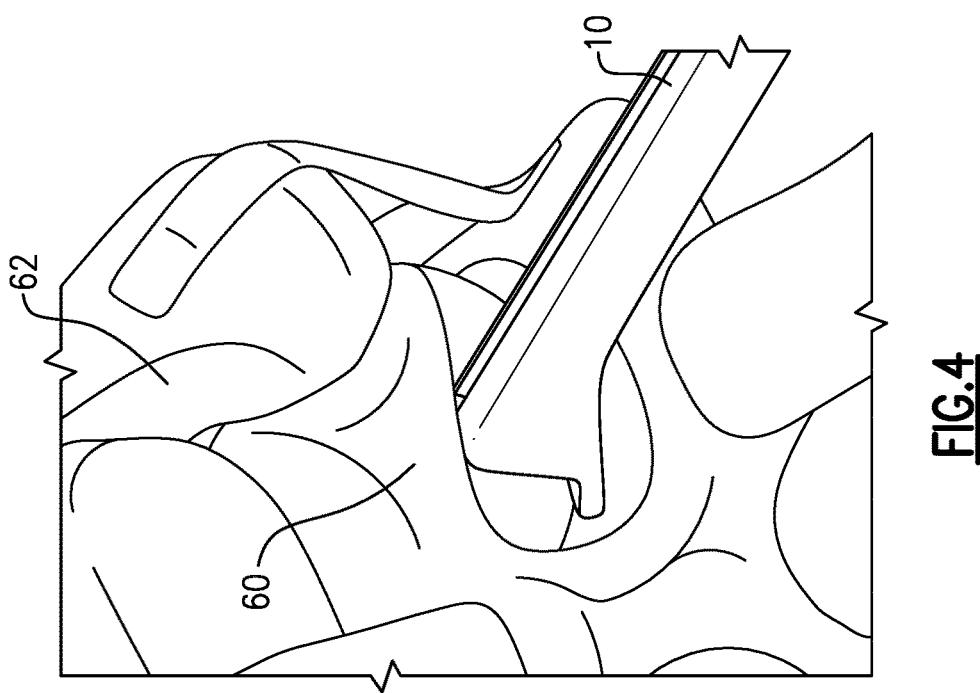

SURGICAL DRILL GUIDE

REFERENCE TO RELATED APPLICATIONS

This application is a continuation of U.S. patent application Ser. No. 15/795,109, filed Oct. 26, 2017, now granted U.S. Pat. No. 10,792,052 issued on Oct. 6, 2020.

BACKGROUND

This disclosure relates to surgical drill guides.

SUMMARY

Surgical drill guides are disclosed that allow a hole to be drilled into a bone at a desired location. A drill bit is inserted into a slot of a drill guide to create a hole in a bone. The drill guide can be used for guiding the drill bit during formation of the hole in the bone. Additionally, a drill guide can have various sizes and shapes, depending on the size and shape of a patient's anatomy, etc. and the type of bone the drill guide is used with.

Drill guides are disclosed herein that include a tapered projection that hooks under a bone to position the drill guide relative to the bone. The drill guide is used to drill a hole in the bone, and a suture anchor is inserted into the hole.

In an embodiment, a drill guide includes an elongated body and a cap at a proximal end of the drill guide. An outer dimension of the cap is greater than an outer dimension of the elongated body. The drill guide includes a slot that extends along a longitudinal axis of the drill guide, and the slot extends through both the elongated body and the cap. The slot extends less than 180° about the longitudinal axis. The slot is uninterrupted along a length of the drill guide. At a distal end of the drill guide, the elongated body includes a planar end surface and a tapered projection that extends at an obtuse angle relative to the planar end surface. The drill guide includes a handle at the proximal end of the drill guide.

In another embodiment, a drill guide includes an elongated body and a cap at a proximal end of the drill guide. The drill guide includes a slot that extends along a longitudinal axis of the drill guide. The slot extends through both the elongated body and the cap. At the distal end of the drill guide, the elongated body includes an end surface and a tapered projection that extends at an angle relative to the end surface.

In another embodiment, a drill system includes a drill guide. The drill guide includes a cap at a proximal end of the drill guide and an elongated slot that extends along a longitudinal axis of the drill guide. The elongated slot extends through both the elongated body and the cap. At the distal end of the drill guide, the elongated body includes an end surface and a tapered projection that extends at an angle relative to the end surface. The drill system includes an insert that is received in the elongated slot of the drill guide. The insert includes elongated body and a cap, and an outer dimension of the cap is greater than an outer dimension of the elongated body. The insert also includes a cannula that extends through the elongated body and the cap. The drill system also includes a drill bit, and the drill bit includes a drill tip, an elongated shaft, and a stop on the elongated shaft. An outer dimension of the stop is greater than an outer dimension of the elongated shaft. A cannula extends through the elongated shaft and the stop. A wire is receivable in the cannula of the insert and the cannula of the drill bit.

In another embodiment, a surgical method includes positioning a tapered projection of a drill guide under a talus, inserting a drill into an elongated slot of the drill guide, and drilling a hole in the talus with the drill.

BRIEF DESCRIPTION OF THE DRAWINGS

FIG. 4 illustrates a schematic perspective view of an embodiment of the drill guide positioned on a talus;

FIG. 5 illustrates a schematic perspective view of an embodiment of the drill guide positioned on a fibula; and FIG. 6 illustrates an ankle joint with two suture anchors.

DETAILED DESCRIPTION

Figure 1:
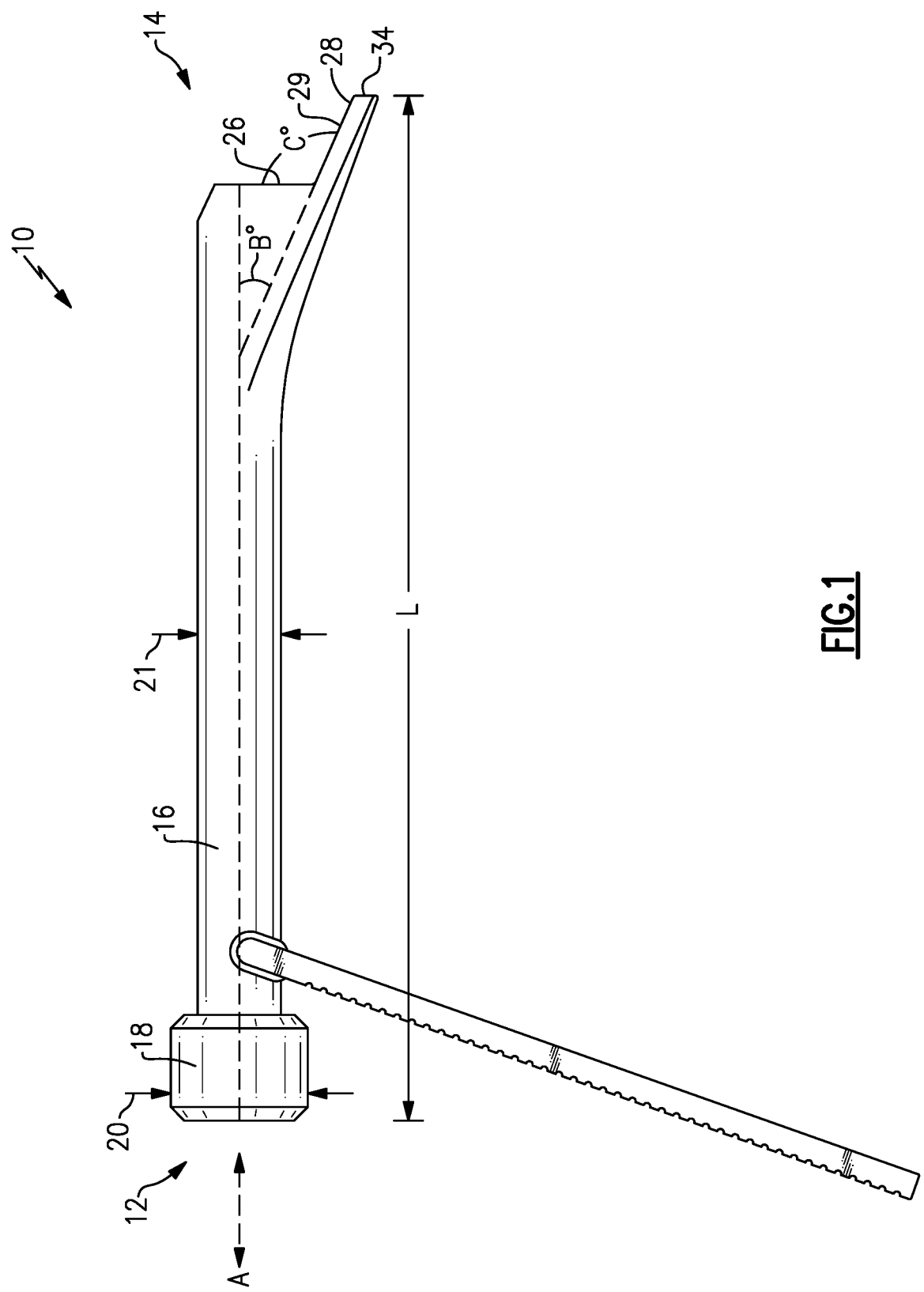
FIG. 1 illustrates a schematic side view of an embodiment of a drill guide.

Surgical drill guides allow a surgeon to accurately drill a hole in a bone a desired location. The hole is drilled in the bone through a slot of the drill guide. A drill guide can be used for guiding a drill during formation of a hole in bone. Additionally, a drill guide can have various sizes and shapes, depending on the size and shape of a patient's anatomy, etc. and the type of bone the drill guide is used with.

Disclosed herein are drill guides including a tapered projection that can hook onto a bone, securing and positioning the drill guide relative to the bone in a desired location prior to drilling. As the projection is tapered, the projection can easily fit behind bones to secure the drill guide relative to the bone. Additionally, the shape of the tapered projection will not accidentally grab unwanted suture or soft-tissue.

In an embodiment, a drill guide includes an elongated body and a cap at a proximal end of the drill guide. An outer dimension of the cap is greater than an outer dimension of the elongated body. The drill guide includes a slot that extends along a longitudinal axis of the drill guide, and the slot extends through both the elongated body and the cap. The slot extends less than 180° about the longitudinal axis. The slot is uninterrupted along a length of the drill guide. At a distal end of the drill guide, the elongated body includes a planar end surface and a tapered projection that extends at an obtuse angle relative to the planar end surface. The drill guide includes a handle at the proximal end of the drill guide.

In another embodiment, a drill guide includes an elongated body and a cap at a proximal end of the drill guide. The drill guide includes a slot that extends along a longitudinal axis of the drill guide. The slot extends through both the elongated body and the cap. At the distal end of the drill guide, the elongated body includes an end surface and a tapered projection that extends at an angle relative to the end surface.

In an embodiment, the slot is uninterrupted along a length of the drill guide. The slot extends less than 180° about the longitudinal axis. In an embodiment, the end surface is a planar end surface. In an embodiment, the tapered projection extends at an angle of about 110° relative to the end surface. In an embodiment, a handle is located at the proximal end of the drill guide. In an embodiment, an outer dimension of the cap is greater than an outer dimension of the elongated body. In an embodiment, the angle between the end surface and the tapered projection is an obtuse angle.

In another embodiment, a drill system includes a drill guide. The drill guide includes a cap at a proximal end of the drill guide and an elongated slot that extends along a longitudinal axis of the drill guide. The elongated slot extends through both the elongated body and the cap. At the distal end of the drill guide, the elongated body includes an end surface and a tapered projection that extends at an angle relative to the end surface. The drill system includes an insert that is received in the elongated slot of the drill guide. The insert includes elongated body and a cap, and an outer dimension of the cap is greater than an outer dimension of the elongated body. The insert also includes a cannula that extends through the elongated body and the cap. The drill system also includes a drill bit, and the drill bit includes a drill tip, an elongated shaft, and a stop on the elongated shaft. An outer dimension of the stop is greater than an outer dimension of the elongated shaft. A cannula extends through the elongated shaft and the stop. A wire is receivable in the cannula of the insert and the cannula of the drill bit.

In an embodiment, the slot is uninterrupted along a length of the drill guide. In an embodiment, the slot extends less than 180° about the longitudinal axis. In an embodiment, the end surface is a planar end surface. In an embodiment, the tapered projection extends at an angle of about 110° relative to the end surface.

In another embodiment, a surgical method includes positioning a tapered projection of a drill guide under a talus, inserting a drill into an elongated slot of the drill guide, and drilling a hole in the talus with the drill.

Methods include performing surgery utilizing the drill guide disclosed herein. In particular, the methods disclosed herein position and secure the disclosed drill guide relative to a bone in a desired location and position prior to drilling the hole.

For example, a method includes positioning the drill guide approximately 45° relative to a bone. An end surface of a tapered projection is positioned at a desired location relative to the bone to hook the drill guide under the bone. An insert is inserted into an elongated slot of the drill guide. A wire is then inserted into a cannula of the insert and into a pre-drilled pilot hole. The insert is then removed from the slot, leaving the wire in the slot. A drill bit is received in the slot of the drill guide such that the wire is received in a cannula of the drill bit. A hole is drilled in the bone. After removing the drill bit and the wire, a suture anchor driver installs a suture anchor in the hole in the bone for use in a surgical repair.

Figure 2:
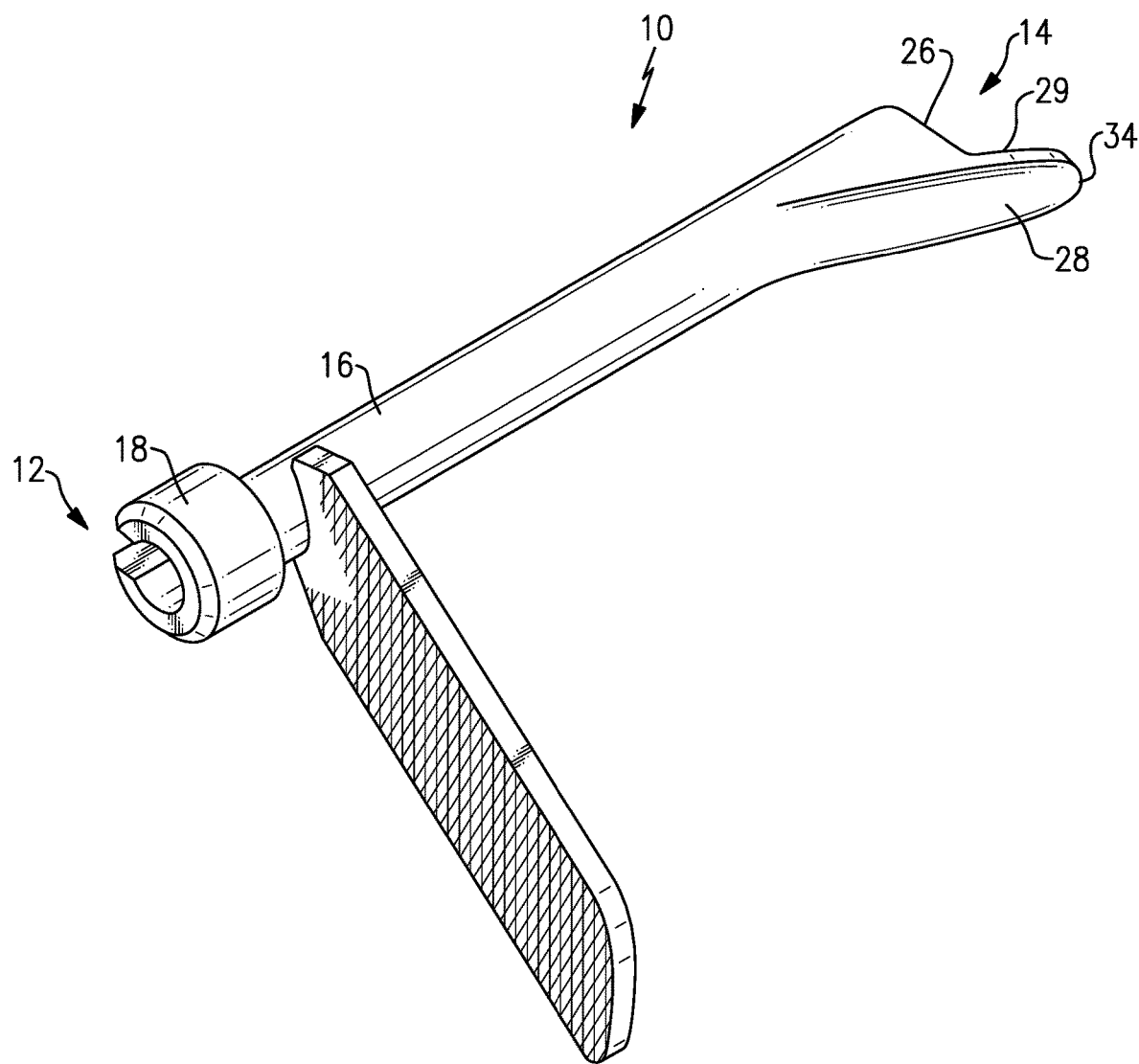
FIG. 2 illustrates a schematic perspective view of an embodiment of the drill guide.

FIGS. 1 and 2 illustrate an exemplary drill guide 10. The drill guide 10 includes a proximal end 12 and a distal end 14. The drill guide 10 includes an elongated body 16 and a cap 18 located at the proximal end 12 of the drill guide 10. An outer dimension 20 of the cap 18 is greater than an outer dimension 21 of the elongated body 16. In one example, the drill guide 10 is made of metal.

A slot 24 extends along a longitudinal axis A of the drill guide 10. The slot 24 extends from the proximal end 12 of the drill guide 10 to the distal end 14 of the drill guide 10 through both the elongated body 16 and the cap 18. The slot 24 has a width W that is uninterrupted along a length L of the drill guide 10. In one exemplary embodiment, the slot 24 extends less than 180° about the longitudinal axis A.

The elongated body 16 includes an end surface 26 located at the distal end 14 of the drill guide 10. In one exemplary embodiment, the end surface 26 is flat and planar. In one exemplary embodiment, the end surface 26 is perpendicular to the longitudinal axis A of the drill guide 10. A tapered projection 28 extends from the end surface 26 of the elongated body 16. In one exemplary embodiment, the tapered projection 28 extends at an angle C° relative to the end surface 26. In one exemplary embodiment, the angle C° is an obtuse angle. As shown in FIG. 1, the obtuse angle C° is defined between the inner planar surface 29 of the tapered projection 28 and the plan end surface 26 of the elongated body 41. In one exemplary embodiment, the angle C° is approximately 110° The tapered projection 28 includes an inner planar surface 29 that engages a bone and a curved end surface 34. The tapered projection 28 extends from the end surface 26 and tapers inwardly towards the curved end surface 34. In one exemplary embodiment, the tapered projection 28 extends at an angle B° relative to the longitudinal axis A. In one exemplary embodiment, the tapered projection 28 extends at an angle of approximately 20° from the longitudinal axis A.

A handle 36 is located at the proximal end 12 of the drill guide 10. The handle 36 can be grasped by a surgeon during a surgical procedure. The handle 36 has a roughened surface and is located between the cap 22 and the tapered projection 28 and closer to the cap 22.

Figure 3:
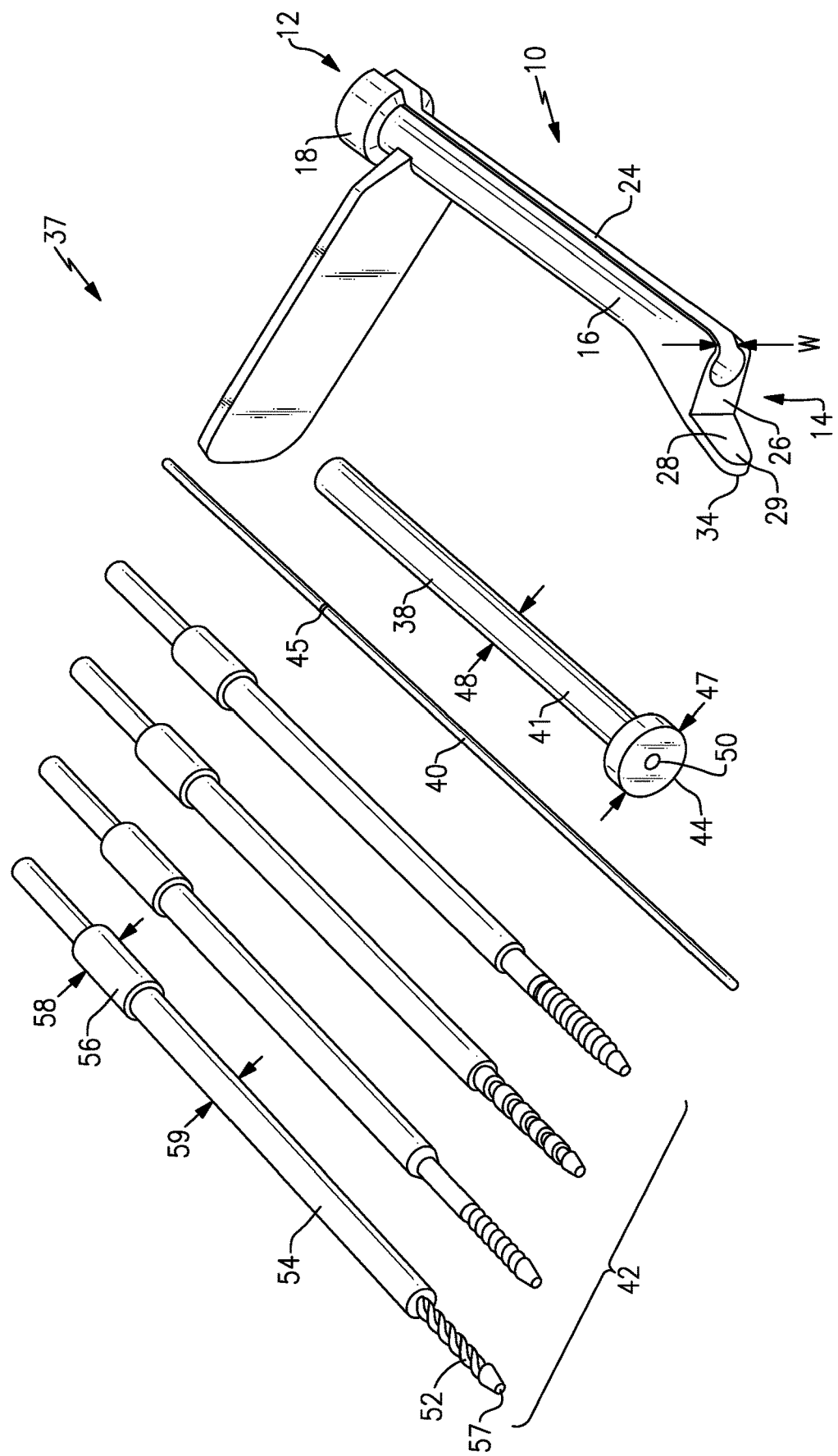
FIG. 3 illustrates a schematic perspective view of an embodiment of a drill system.

As shown in FIG. 3, during a surgical procedure, the drill guide 10 is part of a drill system 37 that also includes an insert 38, a wire 40, and a drill bit 42.

The insert 38 includes an elongated body 41 and a cap 44. In one exemplary embodiment, the elongated body 41 and the cap 44 are both cylindrical and have a cross-section of two concentric circles. An outer diameter 47 of the cap 44 is greater than an outer diameter 48 of the elongated body 41. A cannula 50 extends through the elongated body 41 and the cap 44. However, the elongated body 41 and the cap 44 can have any shape.

In one embodiment, the wire 40 is a Kirschner wire 40 that includes a visual marking 45 that allows for alignment with a portion of the insert 38, such as a line or a recess. The wire 40 is made of stainless steel.

The drill bit 42 includes a drill tip 52, an elongated shaft 54, and a stop 56 on the shaft 54. The drill bit 42 includes a cannula 57. In one exemplary embodiment, the elongated shaft 54 and the stop 56 are both cylindrical and have a cross-section of two concentric circles. An outer diameter 58 of the stop 56 is greater than an outer diameter 59 of the elongated shaft 54. However, the elongated shaft 54 and the stop 56 can have any shape. The cannula 57 extends through the elongated shaft 54 and the stop 56.

As shown in FIG. 4, in one exemplary embodiment, the drill guide 10 is used during an ankle surgery. During surgery, a surgeon grasps the handle 36 of the drill guide 10, and the drill guide 10 is positioned 45° relative to a talus 60. The end surface 26 of the tapered projection 28 is positioned at a desired location relative to a talus 60 so that the tapered projection 28 hooks under the talus 60 at the sinus tarsi. The insert 38 is inserted into the slot 24 of the drill guide 10. The cap 44 of the insert 38 contacts the cap 18 of the drill guide 10 to act as a stop and prevent further insertion of the insert 38. The wire 40 is then inserted into the cannula 50 of the insert 38 and into a pre-drilled pilot hole until the marking 45 of the wire 40 aligns with the cap 46 of the insert 38. The insert 38 can then be removed from the slot 24 of the drill guide 10, leaving the wire 40 in place in the slot 24 of the drill guide 10.

The drill bit 42 is then used to drill a hole in the talus 60. The cannula 56 of the drill bit 42 is aligned with the wire 40, and the drill bit 42 is slid in the slot 24 of the drill guide 10 until the stop 56 of the drill bit 42 engages the cap 18 of the drill guide 10, providing an automated depth stop. The drill bit 42 is then used to drill a hole in the talus 60. After the hole is formed in the talus 60, the drill bit 42 is removed from the slot 24 of the drill guide 10, and the wire 40 can then be removed from the talus 60. A suture anchor driver (not shown) can then be inserted into the slot 24 of the drill guide 10 to install a suture anchor 64 in the hole in the talus 60. Once the suture anchor 64 is installed, the drill guide 10 can be removed from the talus 60.

In another example, the insert 38 and the wire 40 are not used, and the drill bit 42 is inserted directly into the slot 24 of the drill guide 10 to drill the hole in the talus 60.

As shown in FIG. 5, the drill guide 10 can also be used to create a hole in a fibula 62 to receive a suture anchor 66. The tapered projection 28 is positioned in a desired location relative to the fibula 62. A hole is drilled using the steps discussed above, and the suture anchor 66 is inserted into the hole in the fibula 62.

As shown in FIG. 6, in one exemplary embodiment, a suture 68 extends between the two suture anchors 64 and 66 to stabilize the ankle.

As the projection is tapered, the projection can easily fit behind bones to secure and position the drill guide 10 relative to the bone. Additionally, the shape of end surface 26 and the tapered projection 28 will not accidentally grab unwanted suture or soft-tissue.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason, the following claims should be studied to determine the true scope and content of this invention.

What is claimed is:

1. A drill system comprising:
    a drill guide including:
        an elongated body including a planar end surface at a distal end of the elongated body;
        a slot that extends along a longitudinal axis of the drill guide, wherein the slot extends through the elongated body, and the planar end surface at the distal end of the elongated body is perpendicular to the longitudinal axis of the drill guide,
        a tapered projection extending from the distal end of the elongated body of the drill guide and that extends at an obtuse angle relative to the planar end surface of the elongated body, wherein the obtuse angle is defined between an inner planar surface of the tapered projection and the planar end surface of the elongated body, wherein the tapered projection is configured to hook under a talus,
    an insert to be received in the slot of the drill guide, wherein the insert includes an elongated body and an insert cap, and an outer dimension of the insert cap is greater than an outer dimension of the elongated body, and the insert includes a single cannula that extends through the elongated body and the insert cap;
    a drill bit, wherein the drill bit includes a drill tip, a shaft, and a stop on the shaft, and an outer dimension of the stop is greater than an outer dimension of the shaft, and a cannula extends through the shaft and the stop; and
    a wire receivable in the single cannula of the insert and the cannula of the drill bit.

2. The drill guide as recited in claim 1 wherein the slot has a width that is uninterrupted along a length of the drill guide.

3. The drill guide as recited in claim 1 wherein the obtuse angle is 110°.

4. The drill guide as recited in claim 1 including a handle at the proximal end of the drill guide.

5. The drill guide as recited in claim 1 wherein the tapered projection is defined by a first flat surface and an opposing second flat surface, and a width of the tapered projection decreases distally.

6. The drill guide as recited in claim 1 wherein the slot extends less than 180° about the longitudinal axis of the drill guide.

7. The drill system as recited in claim 1 wherein an end of the tapered projection is rounded.

8. A drill guide comprising:
    an elongated body including a planar end surface at a distal end of the elongated body;
    a cap located at a proximal end of the elongated body, and an outer dimension of the cap is greater than an outer dimension of the elongated body;
    a slot that extends along a longitudinal axis of the drill guide, wherein the slot extends through the elongated body, and the planar end surface at the distal end of the elongated body is perpendicular to the longitudinal axis of the drill guide; and
    a tapered projection at the distal end of the drill guide that extends at an obtuse angle relative to the planar end surface of the elongated body, wherein the obtuse angle is defined between an inner planar surface of the tapered projection and the planar end surface of the elongated body, wherein the tapered projection is configured to hook under a talus.

9. The drill guide as recited in claim 8 wherein the slot has a width that is uninterrupted along a length of the drill guide.

10. The drill guide as recited in claim 8 wherein the obtuse angle is 110°.

11. The drill guide as recited in claim 8 including a handle at the proximal end of the drill guide.

12. The drill guide as recited in claim 8 wherein the tapered projection is defined by a first flat surface and an opposing second flat surface, and a width of the tapered projection decreases distally.

13. The drill guide as recited in claim 8 wherein the slot extends less than 180° about the longitudinal axis of the drill guide.

14. The drill guide as recited in claim 8 wherein an end of the tapered projection is rounded.

15. A surgical method comprising:
    hooking a tapered projection of a drill guide under a talus, wherein the tapered projection is located at a distal end of an elongated body of the drill guide, the elongated body has a longitudinal axis and an elongated slot, a proximal end and the distal end of the elongated body are spaced along the longitudinal axis, an inner planar surface of the tapered projection extends at an obtuse angle relative to a planar end surface of the elongated body, and the planar end surface at the distal end of the elongated body is perpendicular to the longitudinal axis of the drill guide;
    inserting a drill into the elongated slot of the drill guide; and
    drilling a hole in the talus with the drill.

16. The method as recited in claim 15 wherein the elongated body and the elongated slot share a longitudinal axis.

17. The method as recited in claim 15 wherein the elongated body has a body length, the elongated slot has a slot length, and the body length is coaxial with the slot length.

18. The method as recited in claim 15 wherein an insert has a cap located at a proximal end of the elongated body, and an outer dimension of the cap is greater than an outer dimension of the elongated body, the method further comprising receiving the insert in the elongated slot of the drill guide and stopping insertion of the elongated body in the slot of the drill guide with the cap.

19. The method as recited in claim 15 further comprising installing a suture anchor in the hole in the talus.

20. The method as recited in claim 19, further comprising positioning the tapered projection relative to a fibula, inserting the drill into the elongated slot of the drill guide, drilling a second hole in the fibula with the drill, installing another suture anchor in the hole in the fibula, and extending a suture between the suture anchor and the another suture anchor to stabilize the ankle.

\* \* \* \* \*

UNITED STATES PATENT AND TRADEMARK OFFICE
CERTIFICATE OF CORRECTION

| | | |
|---|---|---|
| PATENT NO. | : 12,011,183 B2 | Page 1 of 1 |
| APPLICATION NO. | : 17/060195 | |
| DATED | : June 18, 2024 | |
| INVENTOR(S) | : Jorge Acevedo et al. | |

It is certified that error appears in the above-identified patent and that said Letters Patent is hereby corrected as shown below:

On the Title Page

Item (72) Inventors should read: Jorge Acevedo, Naples, FL (US); Peter Mangone, Naples, FL (US); Zachary Day, Naples, FL (US); James McWilliam, Rye, NY (US); Jerome Gulvas, Bonita Springs, FL (US)

Signed and Sealed this
Sixteenth Day of September, 2025

Coke Morgan Stewart
*Acting Director of the United States Patent and Trademark Office*